United States Patent
Foster et al.

(10) Patent No.: US 10,088,083 B2
(45) Date of Patent: Oct. 2, 2018

(54) MULTI LUMEN CO-RADIAL PNEUMATIC CONNECTOR

(71) Applicant: Novartis AG, Basel (CH)

(72) Inventors: James Foster, Santa Ana, CA (US); Mark Alan Hopkins, Mission Viejo, CA (US)

(73) Assignee: Novartis AG, Basel (CH)

( * ) Notice: Subject to any disclaimer, the term of this patent is extended or adjusted under 35 U.S.C. 154(b) by 886 days.

(21) Appl. No.: 14/459,424

(22) Filed: Aug. 14, 2014

(65) Prior Publication Data

US 2016/0045365 A1 Feb. 18, 2016

(51) Int. Cl.
| | |
|---|---|
| *F16L 37/56* | (2006.01) |
| *F16L 21/035* | (2006.01) |
| *F16L 37/084* | (2006.01) |
| *A61M 39/10* | (2006.01) |
| *A61B 90/90* | (2016.01) |
| *A61B 90/96* | (2016.01) |
| *A61B 17/00* | (2006.01) |

(52) U.S. Cl.
CPC .......... *F16L 21/035* (2013.01); *A61B 90/90* (2016.02); *A61B 90/96* (2016.02); *A61M 39/105* (2013.01); *F16L 37/084* (2013.01); *F16L 37/56* (2013.01); *A61B 2017/00477* (2013.01); *A61B 2217/005* (2013.01); *F16L 2201/44* (2013.01)

(58) Field of Classification Search
CPC ...... A61B 90/96; A61B 90/90; A61M 39/105; F16L 37/56
See application file for complete search history.

(56) References Cited

U.S. PATENT DOCUMENTS

| | | | | |
|---|---|---|---|---|
| 4,285,364 | A | * 8/1981 | Hawker | F16L 37/56 137/614.03 |
| 4,619,640 | A | 10/1986 | Potolsky | |
| 4,708,371 | A | * 11/1987 | Elsworth | F16L 37/56 285/120.1 |
| 5,170,841 | A | * 12/1992 | Briet | F16L 37/56 285/921 |
| 5,681,063 | A | * 10/1997 | Bressner | A61M 39/105 285/376 |

(Continued)

FOREIGN PATENT DOCUMENTS

| | | |
|---|---|---|
| DE | 102010032179 A1 | 1/2012 |
| EP | 2537541 A1 | 12/2012 |

(Continued)

OTHER PUBLICATIONS

Prior Art Statement, Apr. 27, 2018.

*Primary Examiner* — David Bochna

(57) ABSTRACT

A multi-lumen surgical utility connector is configured to receive two or more utilities from a surgical utility supplying device. The multi-lumen surgical utility connector may be connected to a utility port of the surgical utility supplying device which supplies two or more utilities. The multi-lumen surgical utility connector may include a Radio Frequency Identification (RFID) tag which identifies the type or model of multi-lumen surgical utility connector. The surgical utility supplying device may determine the type and parameters of utilities to be supplied through the multi-lumen surgical utility connector based on information read from the RFID tag.

8 Claims, 5 Drawing Sheets

(56) References Cited

U.S. PATENT DOCUMENTS

| | | |
|---|---|---|
| 6,649,829 B2 | 11/2003 | Garber et al. |
| 6,897,374 B2 | 5/2005 | Garber et al. |
| 7,137,654 B2 | 11/2006 | Segal et al. |
| 7,394,375 B2 | 7/2008 | Johnson |
| 7,443,296 B2 | 10/2008 | Mezhinsky et al. |
| 7,484,769 B2 | 2/2009 | Domash et al. |
| 7,551,077 B2 | 6/2009 | Raybuck et al. |
| 7,568,619 B2 | 8/2009 | Todd et al. |
| 7,625,014 B2 | 12/2009 | Turner |
| 7,796,040 B2 | 9/2010 | Mezhinsky et al. |
| 7,934,648 B2 | 5/2011 | Charles et al. |
| 8,312,800 B2 | 11/2012 | Turner et al. |
| 8,608,730 B2 * | 12/2013 | Abboud ............... A61M 39/105 606/21 |
| 8,746,290 B2 | 6/2014 | Hopkins et al. |
| 9,227,046 B1 * | 1/2016 | Douglas ............... A61M 39/105 |
| 9,713,503 B2 | 7/2017 | Goldschmidt |
| 2007/0241560 A1 * | 10/2007 | Malone ............... F16L 37/56 285/319 |
| 2008/0103432 A1 | 5/2008 | Sanchez et al. |
| 2009/0118680 A1 | 5/2009 | Goldbrunner et al. |
| 2011/0196291 A1 | 8/2011 | Vischer et al. |
| 2011/0208170 A1 * | 8/2011 | Hafner ............... A61B 90/90 606/1 |
| 2012/0184931 A1 * | 7/2012 | Horn ............... A61M 39/105 604/319 |
| 2013/0015654 A1 | 1/2013 | Gilham et al. |
| 2013/0092244 A1 | 4/2013 | Lee et al. |
| 2013/0092247 A1 | 4/2013 | Lee et al. |
| 2013/0147185 A1 * | 6/2013 | Tsao ............... A61M 39/105 285/120.1 |
| 2013/0245530 A1 * | 9/2013 | Brandl ............... A61M 39/105 604/4.01 |
| 2014/0171855 A1 * | 6/2014 | Mastri ............... A61M 39/105 604/26 |
| 2015/0150546 A1 | 6/2015 | Goldschmidt |
| 2015/0209017 A1 * | 7/2015 | Fleming ............... A61B 90/90 73/864.91 |
| 2015/0327757 A1 * | 11/2015 | Rozenfeld ............... A61B 90/90 600/190 |

FOREIGN PATENT DOCUMENTS

| | | |
|---|---|---|
| WO | 00/61986 A1 | 10/2000 |
| WO | 2007/089201 A1 | 8/2007 |
| WO | 2009/081178 A1 | 7/2009 |
| WO | 2012/170961 A1 | 12/2012 |
| WO | 2016/025964 A1 | 2/2016 |

* cited by examiner

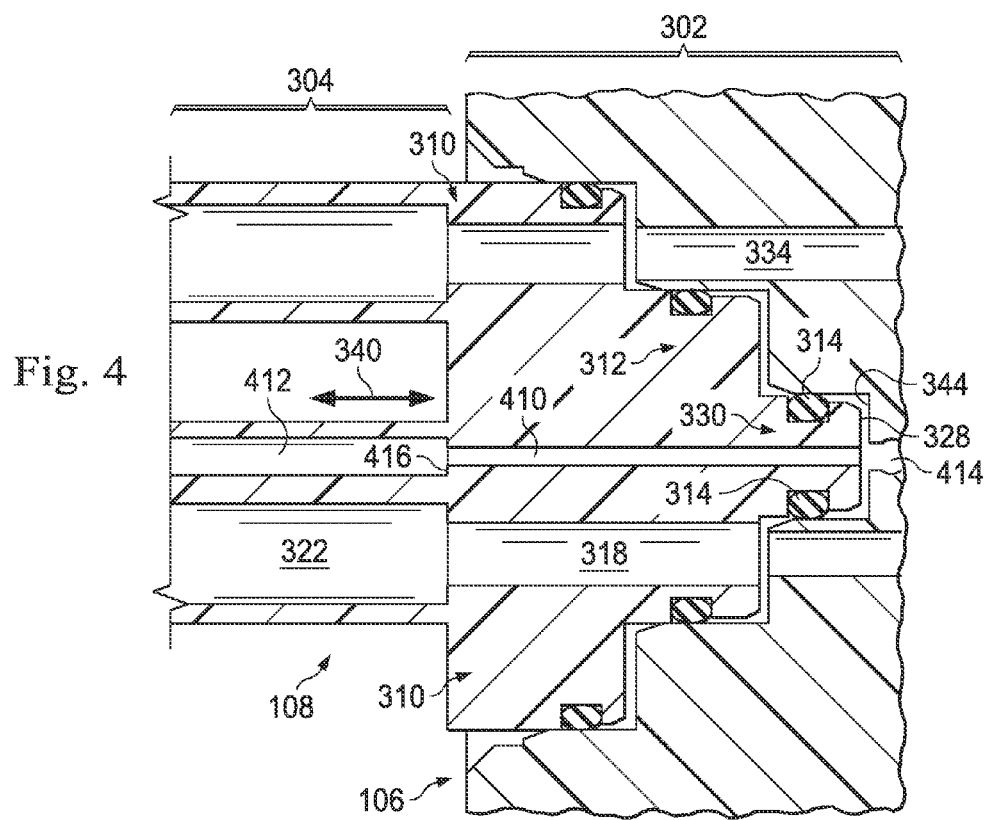
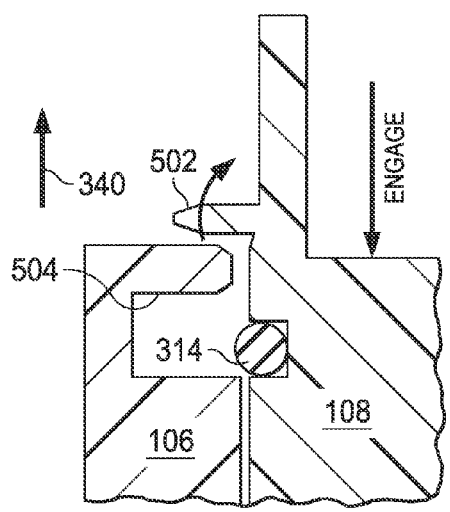
Fig. 5A
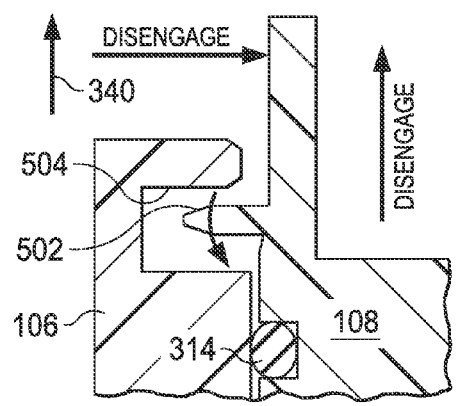
Fig. 5B

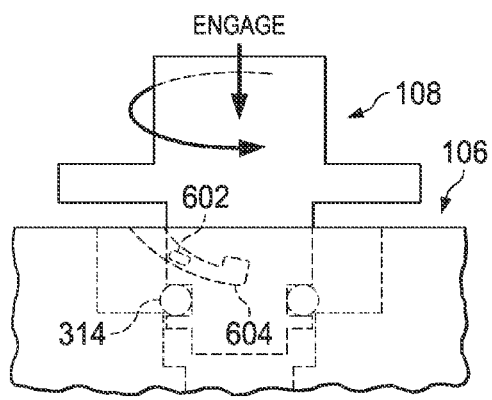
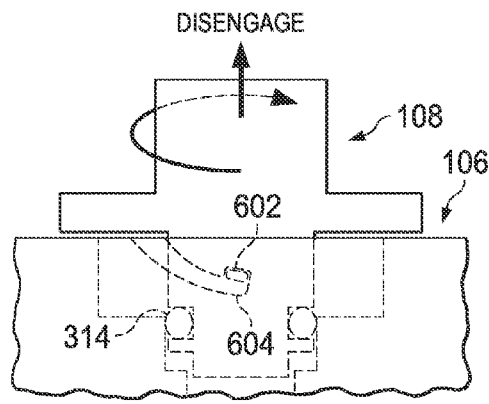
Fig. 6A        Fig. 6B
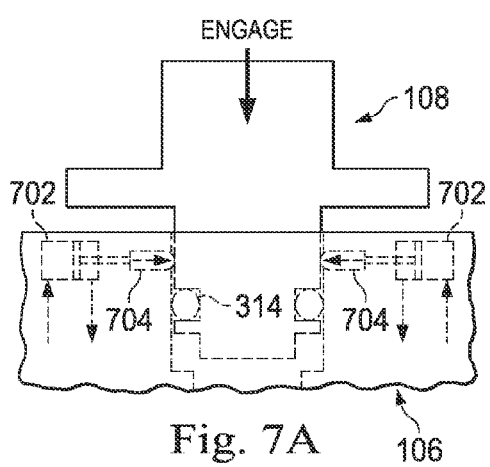
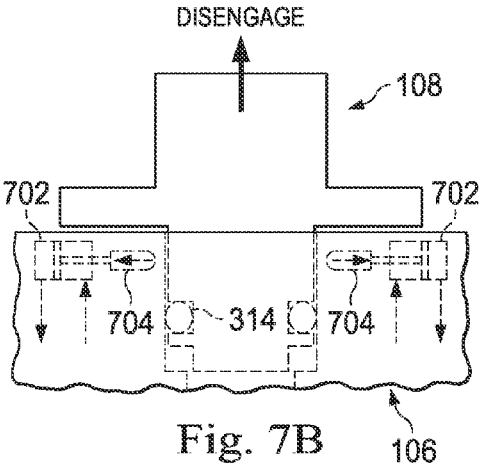
Fig. 7A        Fig. 7B
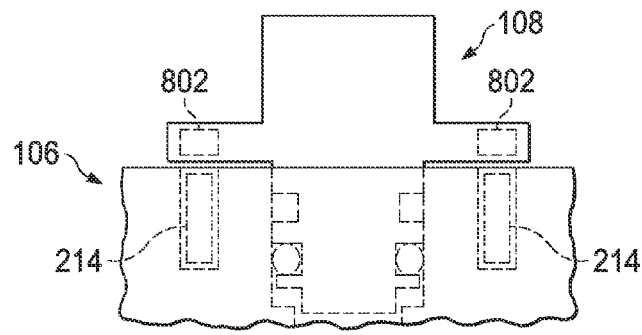
Fig. 8

MULTI LUMEN CO-RADIAL PNEUMATIC CONNECTOR

BACKGROUND

The devices, systems, and methods disclosed herein relate generally to surgical utility connectors, and more particularly, to surgical utility connectors configured to connect a surgical utility supplying device to a surgical implement.

Surgical implements, such as surgical imaging probes, surgical drills, surgical vitrectomy probes, and the like, are connected to a surgical utility supplying device to receive utility, such as laser imaging light, compressed air, fluid, vacuum, or the like. The surgical implements are connected to the surgical utility supplying device via surgical utility connectors.

Some surgical implements, such as pneumatic driven dual acting vitrectomy probes, may require two or more utility inputs to move a diaphragm forward and backward for a cutting operation. The utility inputs to the surgical implement may include pulses of compressed air supplied from two separate utility ports at a utility supplying device. However, it may be inconvenient and troublesome for a user having to make two different connections at two different utility ports when connecting the surgical implement to the surgical utility supplying device and having to remove two different connections at two different utility ports when disconnecting the surgical implement from the surgical utility supplying device.

A known method for preventing misconnections of the two utility inputs includes a male connector and a female connector that differentiate the two utility inputs. For example, the utility supplying device may have a male utility port corresponding to the female connector and a female utility port corresponding to the male connector. O-rings on the respective male connectors or male utility ports create air tight seal between the connectors and the utility ports. However, this kind of arrangement has multiple shortcomings. For example, the O-rings provided on the male utility ports may degrade over time due to exposure to cleaning agents or due to repetitive connection and disconnection. Because the male utility ports are not easily replaceable, the degraded O-rings may cause utility leakage during operations. As another example, when a third utility is required for the surgical implement, it is difficult to further differentiate three utility inputs using merely the male and female connectors.

The present disclosure is directed to devices, systems, and methods that address one or more of the disadvantages of the prior art.

SUMMARY

In an exemplary aspect, the present disclosure is directed to a surgical utility connector configured to connect a surgical implement to a surgical supplying device. The surgical utility connector may include a first connecting region, a first utility channel, a second utility channel, and a second connecting region. The first utility channel may be configured to pass a first utility from the surgical supplying device in a utility flow direction. The first utility channel may extend through a first connecting surface of the first connecting region in the utility flow direction. The second utility channel may be configured to pass a second utility from the surgical supplying device in the utility flow direction. The second utility channel may extend through a second connecting surface of the first connecting region in the utility flow direction. The second connecting region disposed opposite from the first connecting region in the utility flow direction.

In an aspect, the first connecting region is configured to engage a utility port of the surgical supplying device. The second connecting region is configured to engage one or more utility tubes connecting to the surgical implement. The first connecting surface is formed on a first circular step and the second connecting surface is formed on a second circular step. The first and the second circular steps are concentric and the second circular step protrudes further from the second connecting region than the first circular step protrudes from the second connecting region.

In another aspect, the surgical utility connector further may include a third utility channel configured to pass a third utility from the surgical supplying device in the utility flow direction. The third utility channel may extend through a third connecting surface of the first connecting region in the utility flow direction. The surgical utility connector also may include a Radio-Frequency Identification (RFID) tag identifying the surgical utility connector.

In another exemplary aspect, the present disclosure is directed to a surgical system. The surgical system may include a surgical implement, a surgical utility supplying device configured to supply a utility to the surgical implement, and a surgical utility connector configured to connect the surgical implement to the surgical utility supplying device.

The surgical utility connector may include a first connecting region, a first utility channel, a second utility channel, and, a second connecting region. The first connecting channel may be configured to pass a first utility from the surgical supplying device in a utility flow direction. The first utility channel may extend through a first connecting surface of the first connecting region in the utility flow direction. The second utility channel may be configured to pass a second utility from the surgical supplying device in the utility flow direction. The second utility channel may extend through a second connecting surface of the first connecting region in the utility flow direction. The second connecting region disposed opposite from the first connecting region in the utility flow direction.

The surgical utility supplying device may include a utility port and a processor. The utility port may be configured to engage the first connecting region of the surgical utility connector. The processor may be configured to determine a first utility supplied to the first utility channel of the surgical utility connector and a second utility supplied to the second utility channel of the surgical utility connector.

In still another exemplary aspect, the present disclosure is directed to a method including: receiving a surgical implement at a utility port of a surgical utility supplying device via a surgical utility connector, determining, by a processor of the surgical utility supplying device, a first utility and a second utility to be supplied to the surgical implement, and supplying the first utility and the second utility to the surgical implement.

In an aspect, the method also may include detecting an RFID tag disposed in the surgical utility connector. The first utility and the second utility may be determined based on information read from the RFID tag.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 4 illustrates a cross-sectional view of an exemplary surgical utility connector disposed within a utility port according to another aspect consistent with the principles of the present disclosure.

FIGS. 5A and 5B illustrate cross-sectional views of an engagement portion of an exemplary surgical utility connector interacting with a utility port according to an aspect consistent with the principles of the present disclosure.

FIGS. 6A and 6B illustrate cross-sectional views of an exemplary surgical utility connector engaging a utility port according to another aspect consistent with the principles of the present disclosure.

FIGS. 7A and 7B illustrate cross-sectional views of an exemplary surgical utility connector retained at a utility port according to an aspect consistent with the principles of the present disclosure.

FIG. 8 illustrates a cross-sectional view of an exemplary surgical utility connector including a Radio Frequency Identification (RFID) tag detected at a utility port according to an aspect consistent with the principles of the present disclosure.

DETAILED DESCRIPTION

Figure 1:
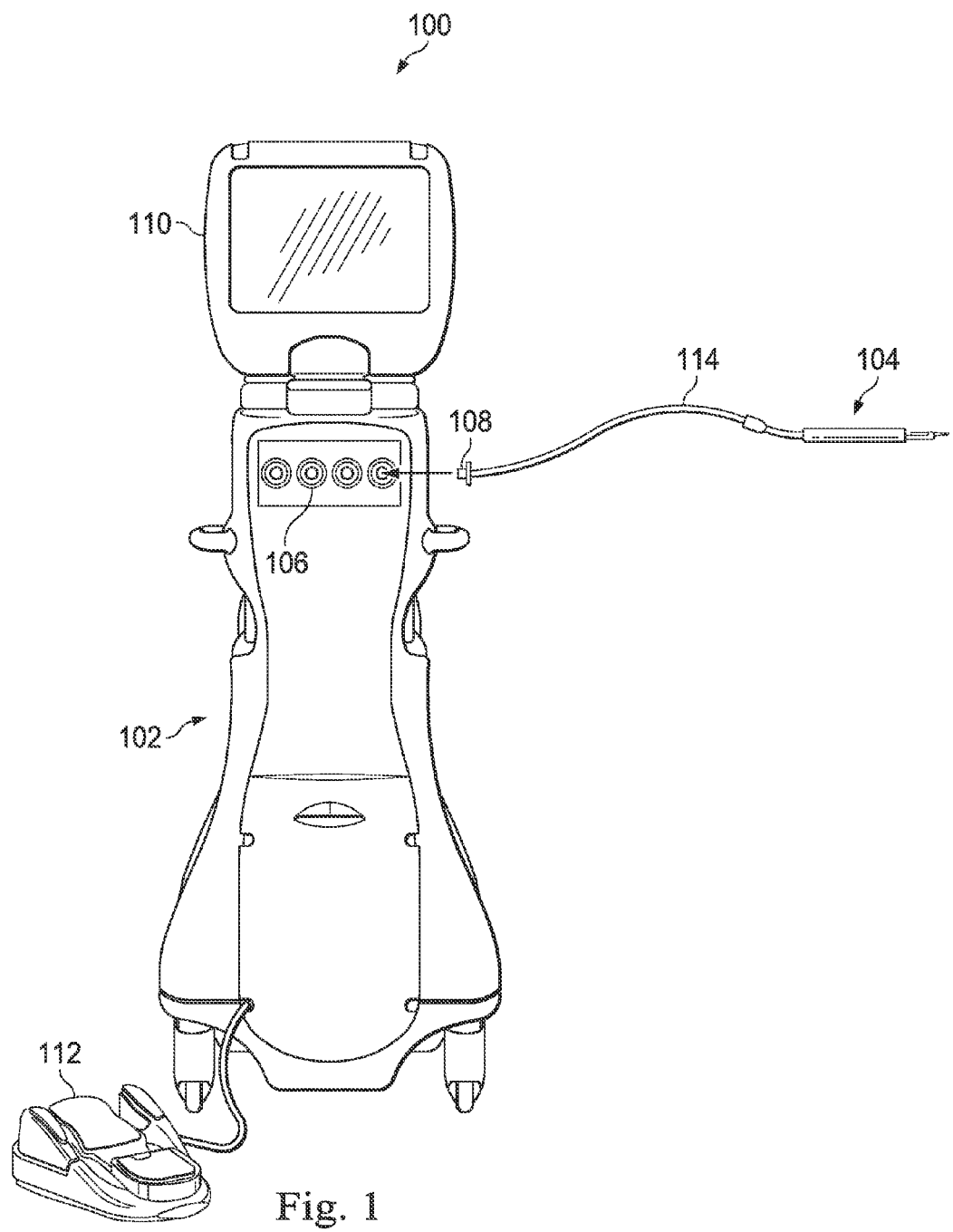
FIG. 1 illustrates a perspective view of an exemplary surgical system according to one embodiment consistent with the principles of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The devices, systems, and methods described herein provide a multi-lumen surgical utility connector configured to carry two or more utilities to or from a surgical utility supplying device. The multi-lumen surgical utility connector may be connected to a utility port of the surgical utility supplying device which supplies two or more utilities. When the surgical utility connector is connected to the utility port of the surgical utility supplying device, the surgical utility supplying device may detect the connection and may retain the multi-lumen surgical utility connector at the utility port. In embodiments disclosed, the multi-lumen surgical utility connector may include a Radio Frequency Identification (RFID) tag which identifies the type or model of multi-lumen surgical utility connector. An RFID detection device may be provided at the utility port of the surgical utility supplying device to detect and read the RFID tag of the multi-lumen surgical utility connector when the multi-lumen surgical utility connector is connected to the utility port. The surgical utility supplying device may determine the types and parameters of utilities to be supplied through the multi-lumen surgical utility connector based on information read from the RFID tag. Because of its design, a user may have to connect only one surgical utility connector to one utility port of the surgical utility supplying device when setting up a surgical implement that requires multiple utilities. In some embodiments, the surgical utility supplying device automatically determines which utilities to supply to respective channels of the multi-lumen surgical utility connector based on information read from the RFID tag included with the multi-lumen surgical utility connector. O-rings or gaskets that provide connection seal may be disposed on or at the multi-lumen surgical utility connectors so they may be easily replaceable to prevent degradation of O-rings or gaskets.

FIG. 1 illustrates an exemplary surgical system, generally designated 100. The surgical system 100 may include a surgical utility supplying device 102 with an associated display screen 110 showing data relating to system operation and performance during a surgical procedure. The surgical system 100 also may include a surgical implement 104 configured to be connected to the surgical utility supplying device 102 via a surgical utility connector 108. The surgical utility supplying device 102 may supply various utilities, such as imaging light, compressed air, vacuum, pressurized liquid, or the like, to various kinds of surgical implements. For example, the surgical utility supplying device 102 may supply laser imaging light to an imaging probe or may supply compressed air to a surgical vitrectomy probe. A user, e.g., a surgeon, may perform surgeries by using the surgical implements. The surgical utility supplying device 102 may include one or more utility ports 106 each configured to output a certain type of utility. Thus, multiple types of utilities may be supplied from the surgical utility supplying device 102 to multiple types of surgical implements 104 at the same time. In some exemplary embodiments, one or more of the utility ports 106 is arranged in a manner that supplied multiple utilities at the same time. For example, a single utility port 106 may supply two different types of compressed air. In another example, the utility port 106 may supply pressurized air and vacuum at the same time. In other example, a liquid is supplied while a waste liquid is received through the same utility port 106. Other utility arrangements and combinations also are contemplated. To accommodate this, certain surgical utility connectors 108 may be multi-lumen surgical utility connectors configured to simultaneously receive multiple utilities from a utility port 106 that supplies multiple utilities.

The utility may be output from the utility port 106 to the surgical utility connector 108 and be carried by a tube fiber or cable (referenced herein as cable 114) to the surgical implement 104. The surgical implements 104 may selectively attach or detach from the utility ports 106 by the surgical utility connectors 108. For example, a surgical implement 104 may be detached from the surgical utility supplying device 102 by detaching the surgical utility connector 108 from the utility port 106. In some embodiments, the surgical utility supplying device 102 detects a connection of a surgical implement 104. Depending on the embodiments, the surgical utility supplying device 102 may allow the supply of utility to the surgical implement 104 after the connection. The exemplary embodiment of the surgical system 100 in FIG. 1 also may include a foot pedal 112 connected to the surgical system 100 for controlling the dispensing of utility from the surgical system 110. In some embodiments, a user controls the dispensing of the utility by selectively pressing and releasing the foot pedal 112.

Figure 2:
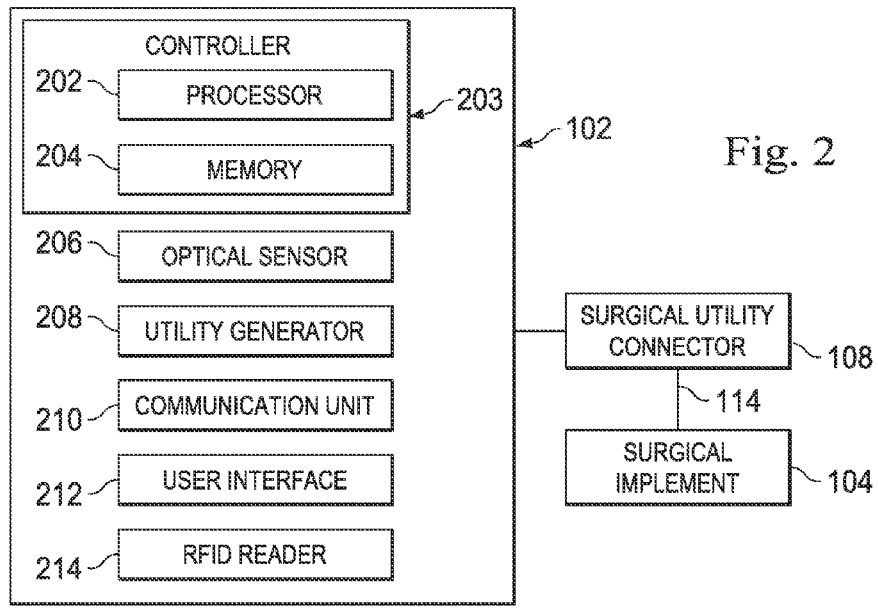
FIG. 2 illustrates a block diagram of an exemplary surgical utility supplying device according to an aspect consistent with the principles of the present disclosure.

FIG. 2 illustrates a schematic diagram of an exemplary surgical utility supplying device, e.g., the surgical utility supplying device 102. The surgical utility supplying device 102 may include a controller 203. The controller may include a processor 202 configured to perform calculation and determination for controlling various operations of the surgical utility supplying device 102. The processor 202 may receive various signal inputs and make various determinations based on the signal inputs. For example, the processor 202 may receive signals from an optical sensor 206 configured to detect a presence of the surgical utility connector 108 to determine a connection status of the surgical implement 104. The processor 202 also may control the display screen 110 to display information regarding the operations of the surgical utility supplying device 102 to convey information to the user.

The controller 203 also may include a memory 204 configured to store information permanently or temporarily for various operations of the surgical utility supplying device 102. For example, the memory 204 may store programs that may be executed by the processor 202 to perform various functions of the surgical utility supplying device 102. The memory 204 also may store various data relating to operation history, user profile or preferences, various operation and surgical settings, and the like. Programs and information stored in the memory 204 may be continuously updated to provide customization and improvement in the operation of the surgical utility supplying device 102. The memory 204 also may include programs and information relating to operational parameters implemented based on the connection status of the surgical utility connector 108 and the utility ports 106.

The surgical utility supplying device 102 also may include the optical sensor 206. The optical sensor 206 may be positioned near a utility port 106 to detect the presence of a surgical utility connector 108 when the surgical utility connector 108 is attached to the utility port 106. The optical sensor 206 may output a voltage signal based on whether the surgical utility connector 108 is detected. For example, the optical sensor 206 may output a low or zero voltage signal when no surgical utility connector is detected and may output a high voltage signal when a surgical utility connector is detected. Other arrangements also are contemplated. The signals output from the optical sensor 206 may be received by the processor 202 and may be utilized to determine the connection status of the surgical implement 104.

The surgical utility supplying device 102 may include a utility generator 208. The utility generator 208 may include motors, light emitting devices, pumps, vacuums, and the like that may generate various utilities, such as pressured liquid, compressed air, vacuum, imaging light, and the like. In some embodiments, the utility generator 208 is connected to an external utility source to receive utility externally. For example, the utility generator 208 may be connected to a vacuum source or an air compressor to receive vacuum or compressed air. The utility generator 208 may supply various utilities to respective utility ports 106.

The surgical utility supplying device 102 may include a communication unit 210. The communication unit 210 may include various communication devices, such as Ethernet card, wi-fi communication device, telephone device, digital I/O (Input-Output) ports or the like, that may allow the surgical utility supplying device to send and receive information to and from other devices. For example, the communication unit 210 may receive input from other surgical devices to coordinate a surgical operation. In another example, the communication unit 210 may transmit and receive messages or notifications, such as email, text, or other messages or notifications to a user's mobile device to notify certain information to the user.

The surgical utility supplying device 102 also may include a user interface 212. The user interface 212 may include user input devices, such as a keyboard, a touch screen, the foot pedal 112, a mouse, a microphone, or the like that allow a user to input instructions to the surgical utility supplying device 212. For example, the user may enter parameters for a utility and operate the foot pedal 112 to dispense the utility to the surgical implement 104. The user interface 212 also may include user output devices, such as a display screen 110, an audio speaker, LED (light-emitting diode) lights, or other visual or tactile signals that convey information to a user. For example, an audio speaker may emit an alarm when a surgical implement 104 is accidentally detached from the surgical utility supplying device 102 during a surgical operation. Thus, the user interface 212 enables a user to interact with the surgical utility supplying device 102 during surgical operations.

Some embodiments of the surgical utility supplying device 102 include an RFID reader 214. The RFID reader 214 may be positioned at or adjacent to the utility port 106 and configured to detect and read RFID tags disposed on, embedded in or otherwise associated with the surgical utility connector 108. In some embodiments, the RFID tag or RFID reader 214 may have or may access a memory that stores information that identifies the type of surgical utility connector or surgical implement connected to the surgical utility connector. For example, when the surgical utility connector 108 is connected to the utility port 106 of the surgical utility supplying device 102, the surgical utility supplying device 102 may use the RFID reader 214 to read the RFID tag associated with the surgical utility connector 108 to determine the type of surgical utility connector or the associated type of surgical implement. Thus, the surgical utility supplying device 102 may determine the type of surgical utility connector or the type of surgical implement that is connected to the utility port 106.

Figure 3:
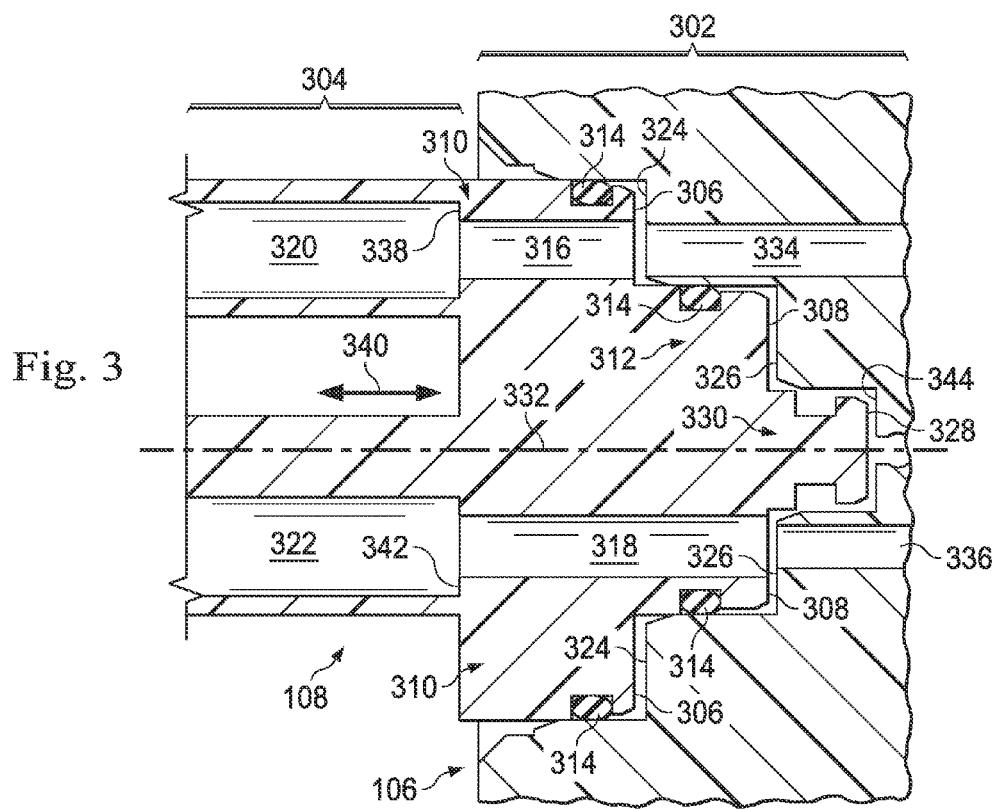
FIG. 3 illustrates a cross-sectional view of an exemplary surgical utility connector disposed within a utility port according to an aspect consistent with the principles of the present disclosure.

FIG. 3 illustrates a cross-sectional view of an exemplary surgical utility connector 108 connected to the utility port 106 according to one embodiment. In this exemplary embodiment, the surgical utility connector 108 is shown as a male-type connector inserted into a female-type utility port

106. The surgical utility connector 108 may include a first connecting region 302 and a second connecting region 304. The first connecting region 302 may be configured to engage with a receiving portion of the utility port 106. The second connecting region 304 may be configured to receive one or more cables 114 (FIG. 1) that are configured to carry various utilities to the surgical implement 104. Some embodiments of the surgical utility connector 108 are formed in part of non-metal material, such as plastic material. Some embodiments of the surgical utility connector 108 have certain elastic characteristics to elastically engage with the utility port 106 and/or the cables 114.

As shown in FIG. 3, the first connecting region 302 includes a first connecting surface 306 provided on a first circular step 310, a second connecting surface provided on a second circular step 312, and a third connecting surface 328 provided on a third circular step 330. The second circular step 312 may be disposed on the first circular step 310 and the third circular step 330 may be disposed on the second circular step 312. The first circular step 310 may have a greater radius than that of the second circular step 312. The second circular step 312 may have a greater radius than that of the third circular step 330.

In some embodiments, the first circular step 310, the second circular step 312, and the third circular step 330 are concentric and share one common central axis 332. IN other embodiments, they are not concentric. The second circular step 312 may protrude farther away from the second connection region 304 than the first circular step 310. The third circular step 330 may protrude farther from the second connection region 304 than the second circular step 312. In the example shown, the circumferential side surfaces of the first circular step 310 and second circular step 312 each include a circumferential groove configured to accommodate elastic rings 314. The elastic rings 314 may be gaskets or consumable O-ring seals configured to provide a tight seal between the surgical utility connector 108 and the utility port 106.

A first utility channel 316 may be formed through the first connecting surface 306 and may extend in a utility flow direction 340 through the first circular step 310. Accordingly, the first utility channel 316 has an opening in the first connecting surface. The first utility channel 316 may have a substantially cylindrical shape. A second utility channel 318 may be formed through the second connecting surface 308 and may extend in the utility flow direction 340 through the second circular step 312 and the first second circular step 310. Accordingly, the second utility channel 318 also has an opening in the second connecting surface 308. The second utility channel 318 may have a substantially cylindrical shape. Non-cylindrical cross-sections are also possible for one or both of the first and second utility channels.

The second connection region 304 may include a first cable receiving interface 320 configured to receive a cable 114 configured to carry a first utility. The first cable receiving interface 320 may connect with the first utility channel 316, such that the first utility may flow from the first channel 316 into the cable 114 received in the first cable receiving interface 320. The first cable receiving interface 320 may have a greater inner diameter than that of the first utility channel 316. In some embodiments, the difference in diameters of the first cable receiving interface 320 and the first utility channel 316 may correspond to a wall thickness of the cable 114. As such, when the cable 114 is inserted into the first cable receiving interface 320, the cable may abut a circular step 338 formed at the interface of the first cable receiving interface 320 and the first utility channel 316. Thus, a seamless cylindrical path may be provided for the flow of the first utility from the first utility channel 316 to the cable 114.

The second connection region 304 also may include a second cable receiving interface 322 configured to receive a cable 114 configured to carry a second utility. The second cable receiving interface 322 may connect with the second utility channel 318, such that the second utility may flow from the second channel 318 into the cable 114 received in the second cable receiving interface 322. The second cable receiving interface 322 may have a greater inner diameter than that of the second utility channel 318. As such, when the cable 114 is inserted into the second cable receiving interface 322, the cable may abut a circular step 342 formed at the interface of the second cable receiving interface 322 and the second utility channel 318. Thus, a seamless cylindrical path may be provided for the flow of the second utility from the second utility channel 318 to the cable 114 received at the second cable receiving interface 322.

The utility port 106 may have a first circular step recess 324, a second circular step recess 326, and a third circular step recess 344 each configured to respectively accommodate the first circular step 310, the second circular step 312, and the third circular step 330 of the surgical utility connector 108. The first circular step recess 324, the second circular step recess 326, and the third circular step recess 344 may be concentric and may have one common central axis 332. The third circular step recess 344 may have a greater recess depth than that of the second circular step recess 326. The second circular step recess 326 may have a greater recess depth than that of the first circular step recess 324.

A first utility supply channel 334 may extend to the first circular step recess 324. The first utility supply channel 334 may be configured to supply the first utility from the utility generator 208 to the utility port 106. A second utility supply channel 336 may extend to the second circular step recess 326. The second utility supply channel 336 may be configured to supply the second utility from the utility generator 208 to the utility port 106.

When the surgical utility connector 108 is inserted into the utility port 106, the three circular steps of the surgical utility connector 108 may be accommodated in the three circular step recesses of the utility port 106. In particular, the elastic rings 314 provided on the circumferential side walls of the first circular step 310 and the second circular step 312 may respectively abut against the inner side wall of the first circular step recess 324 and the inner side wall off the second circular step recess 326. The elastic rings 314 may form a tight seal between the inner side walls of the circular step recesses 324 and 326 and the circumferential side walls of the circular steps 310 and 312 to prevent air or liquid from escaping through the interface between the surgical utility connector 108 and the utility port 106.

FIG. 4 illustrates a cross-sectional view of the surgical utility connector 108 connected to the utility port 106 according to another embodiment. The surgical utility connector 108 and the utility port 106 in FIG. 4 are substantially similar to those in FIG. 3. In FIG. 4, a third utility channel 410 is provided at the third connecting surface 328 to carry a third utility received from the surgical utility supplying device 102. The third utility channel 410 may extend through the third circular step 330, the second circular step 312, and the first circular step 310 in the utility flow direction 340. An elastic ring 314 may be provided at a circumferential wall of the third circular step 330. The elastic ring 314 may provide a tight seal between the circumferential wall of the third circular step 330 and the inner wall of the third circular step recess 344. A third utility supply channel 414 may extend to the third circular step recess 344 of the utility port 106. The third utility supply channel 414 may carry or guide a third utility from the utility generator 208 to the utility port 106.

A third cable receiving interface 412 may be provided at the second connection region 304. The third cable receiving interface 412 may be configured to receive a cable 114 configured to carry a third utility. The third cable receiving interface 412 may connect with the third utility channel 410 such that the third utility may flow from the third utility channel 410 into the cable 114 received in the third cable receiving interface 412. The third cable receiving interface 412 may have a greater inner diameter than that of the third utility channel 410. When the cable 114 is inserted into the third cable receiving interface 412, the cable 114 may abut a circular step 416 formed at the interface of the third cable receiving interface 412 and the third utility channel 410. Thus, a seamless cylindrical path may be provided for the flow of the third utility from the third utility channel 410 to the cable 114.

As shown in FIGS. 3 and 4, the utility port 106 may output two or more kinds of utilities simultaneously and the surgical utility connector 108 may be configured to receive the two or more kinds of utilities simultaneously. For example, two different types of compressed air, e.g., different air pressure, pulsing patterns, and the like, may simultaneously be output from the same utility port 106 to the surgical utility connector to drive a surgical vitrectomy probe. Thus, the user may easily set up a surgical implement that requires two or more utilities by simply connecting the surgical implement to one utility port. Because only one connection is needed, misconnection may be prevented. Further, the elastic rings, e.g., the O-rings, may be provided at the male-type connector, which is easily replaceable when the O-rings degrade due to repetitive use or due to chemical erosion.

FIGS. 5A and 5B illustrate cross-sectional views of an exemplary engagement portion of an exemplary surgical utility connector interacting with a utility port according to an embodiment. As shown FIGS. 5A and 5B, an engagement rib 502 may be provided on a circumferential exterior surface of the surgical utility connector 108. In particular, the engagement rib 502 may surround the circumferential exterior surface at the first circular step 310. The engagement rib 502 may be disposed downstream from the elastic ring 314 of the first circular step 310 in the utility flow direction 310 in a manner that the engagement rib 502 radially protrudes. In another embodiment, the engagement rib 502 may be provided on a circumferential exterior surface at the second connection region 304.

An engagement groove 504 may be provided at an inner surface of the first circular step recess 324. The engagement groove 504 may extend circumferentially around the inner surface of the first circular step recess 324 and may be configured to accommodate the engagement rib 502. For example, as shown in FIG. 5, when the surgical utility connector 108 is inserted into the utility port 106, the engagement rib 502, which may be formed of a plastic material, may flex or bend. As the surgical utility connector 108 is fully inserted into the utility port 106, the engagement rib 502 may be accommodated in the engagement groove 504 to retain the surgical utility connector 108 at the utility port 106.

FIGS. 6A and 6B illustrate cross-sectional views of an exemplary surgical utility connector engaging a utility port according to another embodiment. As shown in FIG. 6, an engagement rib 602 may be provided on an exterior surface of the surgical utility connector 108. In particular, the engagement rib 602 may be provided at the circumferential exterior surface at the first circular step 310. The engagement rib 602 may be disposed downstream from the elastic ring 314 of the first circular step 310 in the utility flow direction 310. The engagement rib 602 may include a protrusion having a substantially oval or round shape. In another embodiment, the engagement rib 502 may be provided on an exterior surface at the second connection region 304.

An engagement groove 604 may be provided at an inner surface of the first circular step recess 324. The engagement groove 604 may be configured to accommodate the engagement rib 602. For example, as shown in FIG. 6, the engagement groove 604 may form a sloped path with a locking portion at an end of the sloped path. When the surgical utility connector 108 is inserted into the utility port 106, the surgical utility connector 108 may rotate to allow the engagement rib 602 of the surgical utility connector 108 to slide in the engagement groove 604. The engagement rib 602 may slide along the sloped path of the engagement groove 604 and may be accommodated in the locking portion of the engagement groove 604 when the surgical utility connector 108 is fully inserted into the utility port 106.

The locking portion may be formed by a bend at the end of the engagement groove 604 and the engagement rib 602 may be retained in the locking portion by a bending corner of the engagement groove 604. As such, in order to disconnect the surgical utility connector 108 from the utility port 106, the surgical utility connector 108 must be pressed slightly toward the utility port 106 to move the engagement rib 602 away from the locking portion of the engagement groove 604 and then the surgical utility connector 108 may be rotated to slide the engagement rib 602 along the sloping path of the engagement groove 604 to disconnect the surgical utility connector 108 from the utility port 106. Thus, the coordination between the engagement rib 602 and the engagement groove 604 may provide a retaining mechanism to retain the surgical utility connector 108 at the utility port 106.

FIGS. 7A and 7B illustrate cross-sectional views of an exemplary surgical utility connector retained at a utility port according to an embodiment. As shown in FIG. 7, a pneumatic retention device 702 may be provided at the utility port 106 to retain the surgical utility connector 108 when the surgical utility connector 108 is connected to the utility port 106. In particular, the pneumatic retention device 702 may include pneumatic cylinders that may be actuated by compressed air to selectively retain and release the surgical utility connector 108.

The pneumatic retention device 702 may include retaining arms that may extend or retract to selectively retain or release the surgical utility connector 108. For example, a retaining arm may have stoppers 704 at a distal end configured to contact an exterior surface of the surgical utility connector 108 to retain the surgical utility connector 108. The pneumatic retention device 702 may be actuated by a user's control or may be actuated automatically to securely retain the surgical utility connector 108 at the utility port 106 before the utilities are supplied to the surgical utility connector 108.

FIG. 8 illustrates a cross-sectional view of an exemplary surgical utility connector including a Radio Frequency Identification (RFID) tag detected at a utility port according to an embodiment. As shown in FIG. 8, an RFID tag 802 may be associated with the surgical utility connector 108. In the examples shown, the surgical utility connector 108 has a ring portion surrounding the body of the surgical utility connector 108 and the RFID tag 802 is embedded in the ring portion. The RFID reader 214 may be provided at the utility port 106 under a surface where the ring portion abuts against when the surgical utility connector 108 is connected to the utility port 106. As such, when the surgical utility connector 108 is connected to the utility port 106, the RFID reader 214 may detect and read the RFID tag 802 positioned proximate to the RFID reader 214. In other embodiments, the RFID tag 802 is adhered to an exterior surface of the connector 108 or otherwise disposed in a manner that cooperates with the RFID reader 214.

In some embodiments, the RFID tag 802 may include an RFID Printed Circuit Board (PCB) storing information related to the surgical utility connector 108. In particular, the RFID tag 802 may identify, for example, the type of the surgical utility connector 108 and the corresponding surgical implement 104. The RFID printed circuit board may include an RFID antenna and circuits configured to receive and respond to signals from RFID readers 214.

Figure 9:
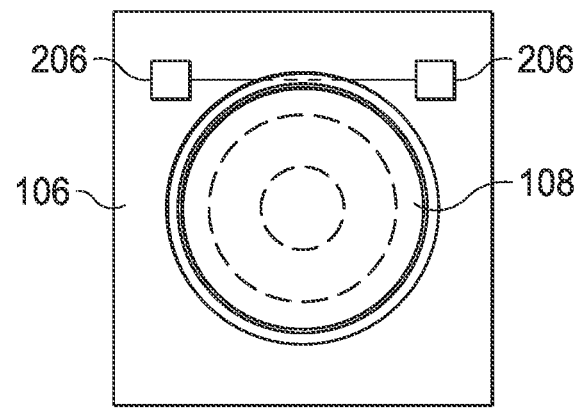
FIG. 9 illustrates a schematic diagram of an exemplary surgical utility connector detected at a utility port according to an aspect consistent with the principles of the present disclosure.

FIG. 9 shows an exemplary surgical utility connector detected at a utility port according to an embodiment. As shown in FIG. 9, the optical sensor 206 may be provided at the utility port 106 to detect a presence of the surgical utility connector 108. In some embodiments, the optical sensor 206 includes a light emitter and a light detector. The light emitter and the light detector may be disposed across a connection position of the surgical utility connector 108. The light emitter may emit a light beam toward the light detector. The light detector may detect the light beam emitted from the light emitter.

When the surgical utility connector 108 is connected to the utility port 106, the surgical utility connector 108 may block the light beam emitted from the light emitter and the light detector may not detect the light beam. The optical sensor 206 may output a low voltage indicating that the surgical utility connector 108 is present. When the surgical utility connector 108 is not connected to the utility port 106, the light beam from the light emitter may be detected by the light detector and the optical sensor 206 may output a high voltage indicating that the surgical utility connector is not present. Thus, the optical sensor 206 may detect the presence or absence of the surgical utility connector 108 at the utility port 106.

Figure 10:
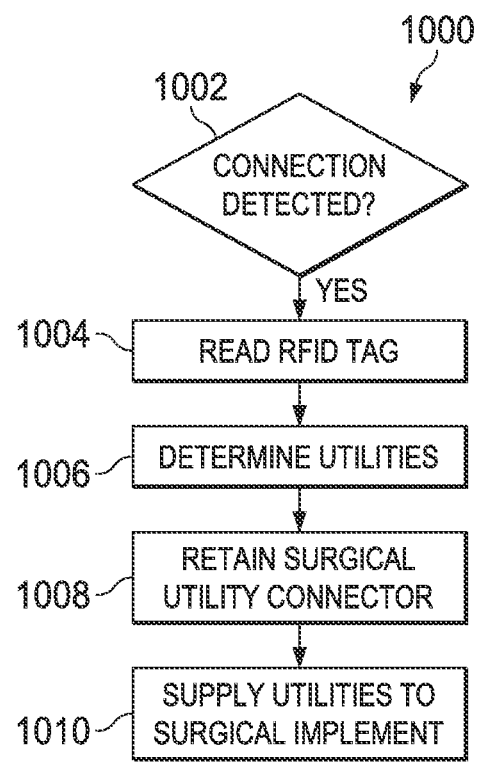
FIG. 10 is a flow chart illustrating a method for supplying utility through a surgical utility connector according to an aspect consistent with the principles of the present disclosure.

FIG. 10 is a flow chart illustrating a method 1000 for supplying utility through a surgical utility connector according to an embodiment. At 1002, surgical utility supplying device 102 may determine whether the surgical utility connector 108 is connected to the utility port 106. For example, the optical sensor 206 may detect a connection of the surgical utility connector 108 by detecting the presence of the surgical utility connector 108 at the utility port 106. When a user plugs the surgical utility connector 108 into a utility port 106, the optical sensor 206 may detect the presence of the surgical utility connector 108 and may output a low voltage indicating the presence of the surgical utility connector 108.

If the surgical utility supplying device 102 determines that the surgical utility connector 108 is connected to the utility port 106, the surgical utility supplying device 102 may read an RFID tag 802 embedded in the surgical utility connector 108 at 1004. The RFID tag 802 or the surgical utility supplying device 102 may have a memory that stores identity information and a description of the type of surgical utility connector that may represent the type of associated handpiece or surgical implement. In some aspects, the RFID tag may store instrument identification or parameters of the surgical implement. In particular, the RFID tag 802 or the surgical utility supplying device 102 may store surgical parameters, such as preferred range of flow rate, pressure, intensity of utility for a specific surgical implement.

At 1006, the surgical utility supplying device 102 may determine the utilities to be supplied to the surgical utility connector 108 based on the information read from the RFID. For example, the RFID tag 802 may indicate that the surgical utility connector is for supplying two types of compressed air, e.g., two different utility output parameters, to a surgical implement. In particular, the parameters of two types of compressed air also may be determined from the information read from the RFID tag 802. For example, the pressure level, pulsing pattern, and other parameters for each of the two types of compressed air may be determined from the information read from the RFID tag 802. The surgical utility supplying device 102 may reference a data table to determine the utility parameters for the identified surgical utility connector 108 or surgical implement 104.

The RFID scanner/reader 214 (FIG. 2) may be configured to detect and read the RFID tag 802 when the surgical utility connector 108 is connected to the utility port 106. Thus, the surgical utility supplying device 102 may read the RFID tag 802 of the surgical utility connector 108 to determine the type of surgical implement 104 connected to the corresponding surgical utility connector 108. For example, the RFID tag 802 may have a memory that stores the identification and description of the surgical utility connector 108 and its corresponding surgical implement 104. This information may be communicated to the surgical utility supplying device 102 for operation. Alternatively, the RFID tag 802 may provide an identifying indicator, and the surgical utility supplying device 102 may look up the identification and description based on the indicator.

At 1008, the surgical utility supplying device 102 may retain the surgical utility connector 108 at the utility port 106. For example, a pneumatic retention device 702 may be used to retain the surgical utility connector 108 at the utility port 106. In an embodiment, 1008 may be implemented in response to a user's command. In an embodiment, 1008 may be implemented automatically before utilities are output from the utility port 106.

At 1010, the surgical utility supplying device 102 may supply the utilities to the surgical implement 104 via the surgical utility connector 108. In particular, the surgical utility supplying device 102 may supply the utilities with specific parameters as determined from the information read from the RFID tag 802 imbedded in the surgical utility connector 108.

Accordingly, the above embodiments provide a system or method for implementing a multi-lumen surgical utility connector to simultaneously provide multiple utilities from a surgical utility supplying device to a surgical implement that requires multiple utilities. In particular, the system or method may allow a utility port to output multiple utilities to a multi-lumen surgical utility connector. As such, a user only has to connect the surgical implement to one utility port to set up the surgical implement. Further, an RFID tag may be provided at the surgical utility connector to indicate the types and parameters of utilities to be supplied to the surgical implement.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A surgical utility connector configured to connect a vitrectomy probe to a surgical supplying device, the surgical utility connector comprising:
   a first connecting region;
   a first utility channel extending through a first step of the first connecting region;
   a second utility channel extending through a second step of the first connecting region;
   further comprising a third utility channel extending through a third step of the first connecting region;
   a Radio-Frequency Identification (RFID) tag embedded in the surgical utility connector with information identifying the surgical utility connector;
   wherein the first and second steps on the first connecting region are configured to mate with complementary receiving recesses on an opposing second connecting region to form a connection between the vitrectomy probe and the surgical supplying device;
   wherein the second step protrudes further into the second connecting region than the first step when the first and second connecting regions are connected;
   wherein the first and second connecting regions each convey a separate pneumatic air channel from the surgical supplying device to the vitrectomy probe.

2. The surgical utility connector of claim 1,
   wherein the first connecting region is configured to interface with a utility port of the surgical supplying device; and
   wherein the second connecting region is configured to interface with one or more utility tubes connecting to the vitrectomy probe.

3. The surgical utility connector of claim 1, wherein the first step is a circular step and the second step is a circular step concentric with the first step.

4. The surgical utility connector of claim 1, wherein the first step comprises a first seal disposed on a side wall of the first step and the second step comprises a second seal disposed on a side wall of the second step.

5. The surgical utility connector of claim 1, wherein the second connecting region comprises a first tubing interface configured to connect a first utility tube to the first utility channel and a second tubing interface configured to connect a second utility tube to the second utility channel.

6. The surgical utility connector of claim 2 further comprising a ring-shape engagement rib protruding from an exterior surface of the surgical utility connector, wherein the ring-shape engagement rib is configured to be accommodated in a circular groove of the utility port of the surgical supplying device when the surgical utility connector is connected to the utility port.

7. The surgical utility connector of claim 2 further comprising an engagement nob protruding from an exterior surface of the surgical utility connector, wherein the engagement nob is configured to slide along and be accommodated in an engagement groove of the utility port of the surgical supplying device when the surgical utility connector is connected to the utility port.

8. The surgical utility connector of claim 1, wherein the first and second steps protrude farther into the second connecting region than the third step.

* * * * *